United States Patent
Kehr et al.

(10) Patent No.: US 8,291,601 B2
(45) Date of Patent: Oct. 23, 2012

(54) REUSABLE METAL BLADE HANDLE

(75) Inventors: Pankaj Kehr, Haryana (IN); Klaus Ruettgers, Solingen (DE)

(73) Assignee: Pankaj Kehr, Gurgaon (IN)

( * ) Notice: Subject to any disclaimer, the term of this patent is extended or adjusted under 35 U.S.C. 154(b) by 145 days.

(21) Appl. No.: 11/887,465

(22) PCT Filed: Mar. 31, 2006

(86) PCT No.: PCT/IN2006/000111
§ 371 (c)(1),
(2), (4) Date: Mar. 1, 2010

(87) PCT Pub. No.: WO2006/103701
PCT Pub. Date: Oct. 5, 2006

(65) Prior Publication Data
US 2010/0152755 A1    Jun. 17, 2010

(30) Foreign Application Priority Data
Apr. 1, 2005    (IN) .............................. 851/DEL/2005

(51) Int. Cl.
*A61B 17/32*    (2006.01)
*B26B 5/00*    (2006.01)
(52) U.S. Cl. .............................. 30/329; 30/340; 606/167
(58) Field of Classification Search .................... 30/329, 30/340, 162, 335, 399, 337, 168; 606/167, 606/166, 170, 171, 184, 185
See application file for complete search history.

(56) References Cited

U.S. PATENT DOCUMENTS

| | | | | |
|---|---|---|---|---|
| 1,368,842 A * | 2/1921 | Roeling | | 30/289 |
| 1,578,538 A * | 3/1926 | McCain | | 30/337 |
| 1,647,546 A * | 11/1927 | Schmidt, M. | | 30/157 |
| 1,973,569 A * | 9/1934 | Kurtz | | 606/208 |
| 2,854,005 A * | 9/1958 | Vido | | 606/174 |
| 3,636,629 A * | 1/1972 | Baun | | 30/94 |
| 4,551,917 A * | 11/1985 | Walker | | 30/161 |
| 5,015,252 A * | 5/1991 | Jones | | 606/205 |
| 5,330,494 A * | 7/1994 | van der Westhuizen et al. | | 606/167 |
| 6,941,661 B2 * | 9/2005 | Frazer | | 30/160 |
| 2003/0212057 A1 * | 11/2003 | Rudolf et al. | | 514/211.08 |
| 2006/0053639 A1 * | 3/2006 | Nakanishi | | 30/329 |
| 2006/0200996 A1 * | 9/2006 | Pearman | | 30/158 |

FOREIGN PATENT DOCUMENTS

| | | |
|---|---|---|
| EP | 0 588 220 | 3/1994 |
| GB | 1910 02812 | 0/1910 |
| GB | 2 255 926 | 11/1992 |
| GB | 2 296 213 | 6/1996 |

* cited by examiner

*Primary Examiner* — Ghassem Alie
(74) *Attorney, Agent, or Firm* — Ladas & Parry LLP

(57) ABSTRACT

The present invention relates to a reusable metal blade handle. More particularly, the present invention relates to a reusable metal blade scalpel handle with safety features provided therein which are also usable across a wide range of blades. In particular, the present invention has application for reusable metal surgical scalpels, providing the facility of a uniform handle type across a variety of blade types.

6 Claims, 5 Drawing Sheets

SAFE LOCK SCALPEL (1)

BLADE LOCATE ARM (2)

BLADE LOCK ARM (3)

REUSABLE METAL BLADE HANDLE

FIELD OF THE INVENTION

The present invention relates to a reusable metal blade handle. More particularly, the present invention relates to a reusable metal blade scalpel handle with safety features provided therein which are also usable across a wide range of blades. In particular, the present invention has application for reusable metal surgical scalpels, providing the facility of a uniform handle type across a variety of blade types.

BACKGROUND OF THE INVENTION

Blades of various types are known for different applications. For example, in the field of hobby and crafts, it is known to use fine edged blades for cutting and shaping of hard materials such as wood, cardboard, Bristol Board, and other similar such materials according to the desired patterns.

Similarly, the use of metal scalpels in surgery is well known. Till the early part of the 20th century, such scalpels comprised of single piece metal surgical knives which required repeated sharpening to ensure reuse.

Around 1915 a system of a disposable blade which could be fitted on a metal handle was created in the USA. This system, the fitment dimensions of which were harmonised internationally in 1985 by the International Standards Organisation (Standard No. ISO 7740: 1985—Instruments for Surgery—Scalpels with detachable blades—Fitting dimensions) is the system which is currently used worldwide. However, this system has several design weaknesses, which puts both the user and the patient at risk. The risks arise due to:
1. Difficulty in fitting and removal of the blade on the handle. As a result, nursing and surgical personnel who use the scalpel are at a risk of injury even when they have been trained in methods of fitting and removal of blades on the handle.
2. Another problem associated with such designs is that the risk of accidental injury by a blood-contaminated blade is high when removing the blade. This is because it is necessary to use a finger to lift the heel of the blade thereby bringing the fingers close to the cutting edge of the blade.
3. A third problem is that fitting and removal of blades is often hampered by inaccurate fitment dimensions.
4. Blades are known to break during fitting on and removing from the handle.
5. Blades often will break during use on a patient, especially in arthroscopy procedures, where the blade encounters hard tissue or bone.

Scalpels have also been used by hobby enthusiasts as well as in industry for various purposes. For example, it is common for hobbyists to use scalpels to devise models using wood. It is also known to use such scalpels in industry to ensure delicate cuts in material such as polymeric material. However, industrial users or hobbyists often are not trained in the techniques of fitting and removing blades from handles and therefore run the risk of being cut during use. Another problem faced in industrial or hobby applications is that the blade is subjected to heavy lateral forces as blades are also used for scraping, whittling and chiseling. Blades will therefore frequently break thereby increasing the chance of injury.

Blades with a reinforced back in the form of a rib are available which are stronger but which are nevertheless known to break during use or during transportation. These blades are up to four times more expensive than standard surgical blades.

During the 1970's disposable scalpels were introduced in the market. Though their introduction eliminated the risk associated with fitting on and removing blades from handles they were not widely accepted, especially by surgeons, due to the lack of weight and feel of the disposable scalpel compared to the traditional metal handle. A second strong disincentive is the high cost of disposable scalpels. In many countries disposable scalpels are not in use.

More recently "blade remover units" have been introduced but are expensive. Such blade removal units are also not an integral part of the design of a scalpel, which is considered necessary for a device to be rendered safe. Their usage also means one more device being introduced into the sterile field (they are non-sterile) and does not eliminate the need for a sharps disposal container. In many countries "blade remover unit" are not in use.

In recent years, due to OSHA, USA regulations a proliferation of safety scalpels have been introduced into the market. The very first devices that were introduced were essentially disposable scalpels with engineered safety features. Again these were not widely accepted, despite the pressure of the regulations, for the very same reasons i.e. lack of weight and feel of a traditional scalpel metal handle, high cost of each device, unfamiliarity with features, and the training required to use them.

Another important feature in surgery over the past few years has been concern over the possibility of infection in operating personnel from patients suffering from highly contagious diseases such as AIDS, hepatitis, or other related contagious diseases. It is therefore important to be able to either provide disposable scalpels or provide for handles where the blade can be easily disassembled after use and the scalpel handle cleaned thereafter.

A second generation of safety scalpels, recognising the importance of the weight of a traditional scalpel metal handle, have either added weight to their plastic safety scalpels or have introduced a metal handle with proprietary system of fitment. To these handles only a blade cartridge with proprietary fitment system can be fitted. Surgical Blades with the internationally accepted and used ISO 7740: 1985 system cannot be fitted on these handles. Though these handles may have the weight, comparable to a traditional metal handle, they do not have the feel of reusable one due to their bulk or sliding sheaths etc. These are also the most expensive scalpels available in the market.

OBJECTS OF THE INVENTION

The main object of the invention is to provide a metal handle for blades which has uniform application irrespective of the type of blade being used, i.e. with greater universality of use in both hobby and crafts as well as in surgery irrespective of the blades being used.

Accordingly, it is necessary to provide a metal handle for a scalpel which has a greater degree of universality of application in terms of both blade types as well as for industrial and hobby use. While providing such scalpel handles, safety is a paramount along with cost, particularly in surgical use.

SUMMARY OF THE INVENTION

Accordingly, the present invention provides an universal blade handle comprising a blade holding arm and a blade lock arm, the blade holding arm being provided with a plurality of receiving means to receive a pivot pin, a blade lock pin, a first blade locating pin, a second blade locating small pin, a stopper pin, and a locking means.

In one embodiment of the invention, the blade lock pin, the first blade locate pin and the second blade locate pin comprise pins with different shapes and sizes and are provided at front end of blade locating arm to form a blade seat to locate the blade.

In another embodiment of the invention, the receiving means comprise one or more holes drilled and tapped into the blade holding arm.

In another embodiment of the invention, the blade locking arm functions as a lock.

In another embodiment of the invention, the receiving means comprise straight holes or half cut slots enabled to receive the corresponding pins.

In another embodiment of the invention, the blade lock arm is pivotably mounted on the blade locating arm through a pivot pin.

In another embodiment of the invention, the blade lock arm is movable from a first position to a second position wherein it is stopped by a stopper pin to enable the blade seat to be fully open for insertion of blade.

In another embodiment of the invention, the lock arm is movable in an anti-clockwise direction in order to enclose the blade with proper alignment with respect to the blade locate arm.

In another embodiment of the invention, the tail portion of lock arm is engageable with the lock pin In another embodiment of the invention, the blade locate arm is provided with thumb griff lines.

BRIEF DESCRIPTION OF THE ACCOMPANYING DRAWINGS

DETAILED DESCRIPTION OF THE INVENTION

The present invention provides a improved surgical scalpel handle which enables incorporation of a wider range of scalpel blades to a handle which is safer to use than the currently internationally used ISO 7740: 1985 system of blades and scalpel handle fitment. The handle of the invention the following advantages:

1. Any standard blade with ISO 7704: 1985 fitment dimension can be used.
2. Allows the user to choose from carbon and stainless steel blades.
3. On the handle are pins on which a blade can be dropped down to fit or dropped off to remove and dispose. No sliding, pulling, pushing, bending, lifting, struggling. Hands away from the edge at all times. See pictures.
4. Blades are firmly clamped into place, obviates the possibility of blade coming off the handle.
5. The clamping should be such that it reinforces the blade and reduces the risk of blades breaking or flexing and distortion and ensures that the blade is steady during use. In the present invention, this is achieved by providing clamping of the blade between the two locked arms of the handle.
6. The device can be disassembled to facilitate that each component can be thoroughly cleaned.
7. The device can be cleaned following the same validated procedures for cleaning of currently used reusable metal handles.
8. The use of expensive reinforced back blades are avoided.

The handle of the present invention provides several advantages in terms of removal of blades therefrom. Removal of the blade requires gripping the blade with a forceps or similar such device and lifting the blade heel at the lower end of point with the tip of the finger and sliding the blade away from the handle. This is appreciably simpler than methods of removal in traditional blade handles. As can be appreciated the novel construction of the handle ensures that the finger of the user does not come in contact with the cutting edge of the blade.

The manner of handling of a blade prior to use can determine how effectively it performs during use. There are a number of methods by which the cutting edge of a blade can become damaged once removed from its protective foil packet.

For example, when removing a blade form the protective packet the blade must not be dropped into a metal bowl or container since this can reduce the initial keenness of the cutting edge even before it is fitted to the handle. Similarly, when a forceps or needle holder is used to remove the blade from its protective packet the blade must not be gripped across the cutting edge.

The blade is fitted to the surgical handle using the following procedure.

The blade is gripped with a forceps, or similar device while avoiding contact with cutting edge. The handle is held in the free hand with bayonet fitting uppermost.

Figure 1:
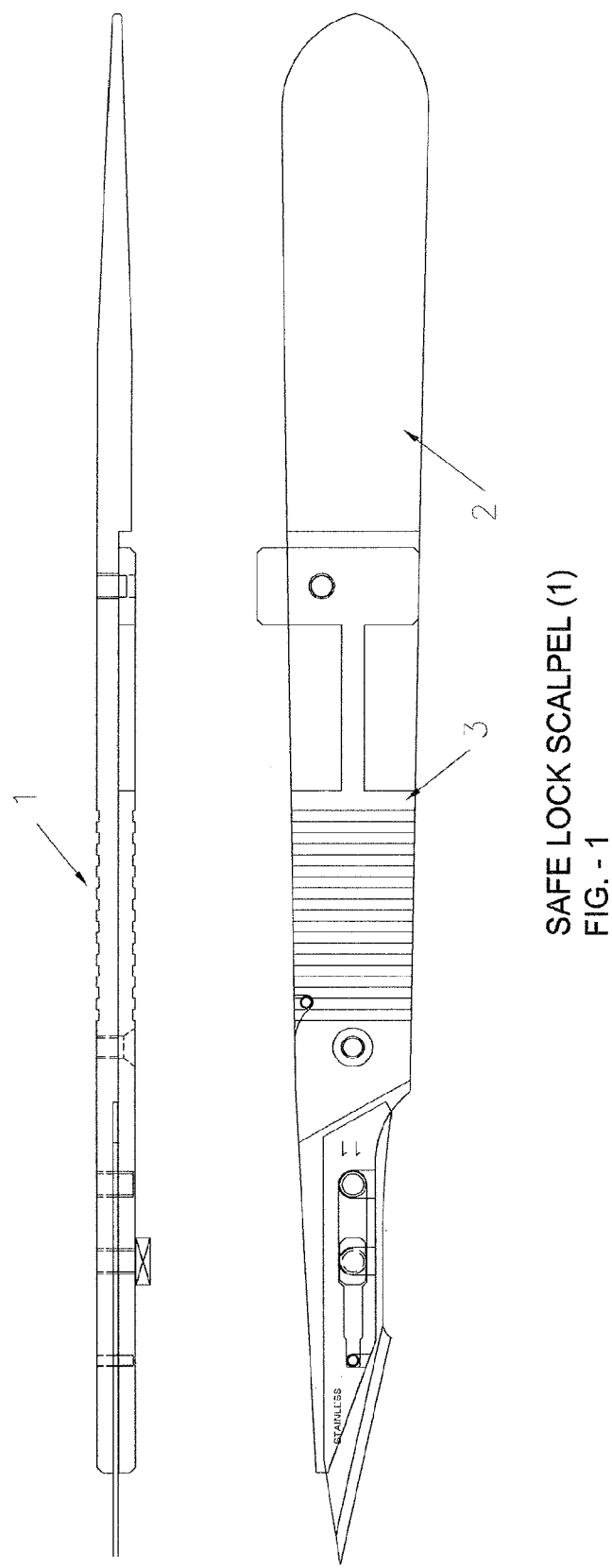
FIG. 1 is a schematic representation of the handle of the invention fitted with a detachable scalpel blade in a ready to use condition.

The following description explains the invention better when read with reference drawings, FIG. 1 is a schematic representation of the handle of the invention fitted with a detachable scalpel blade in a ready to use condition.

Figure 2:
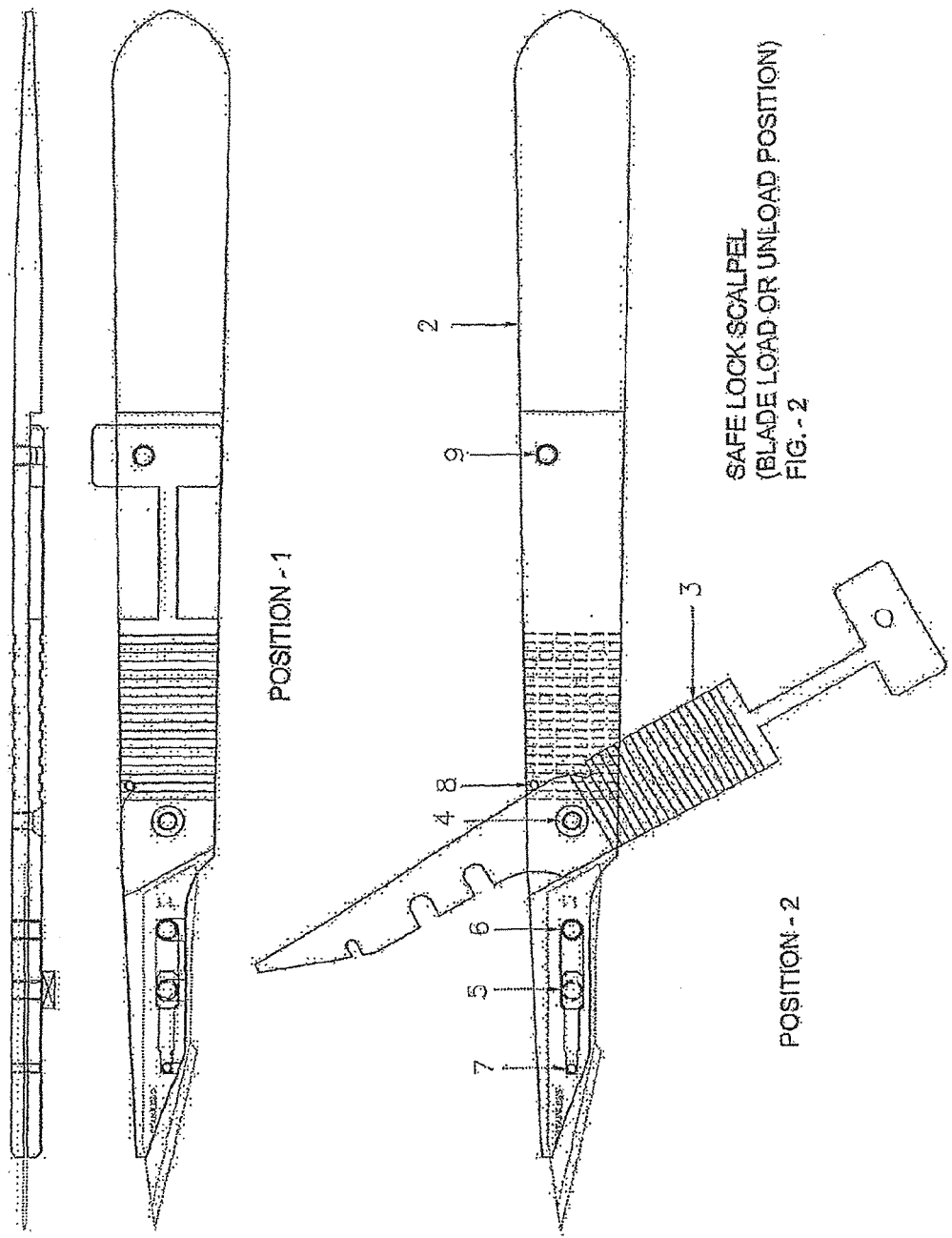
FIG. 2 is a schematic representation of an unlocked reusable metal scalpel handle of the invention showing the various components thereof.

FIG. 2 is a schematic representation of an unlocked reusable metal scalpel handle of the invention showing the various components thereof as given below and indexed using reference numbers i. Blade locate arm (2)
ii. Blade lock arm (3)
iii. Pivot pin (4)
iv. Blade lock pin (5)
v. Blade locate big pin (6)
vi. Blade locate small pin (7)
vii. Stopper pin for blade lock arm (8)
viii. Lock pin for blade lock arm (9)

Figure 3:
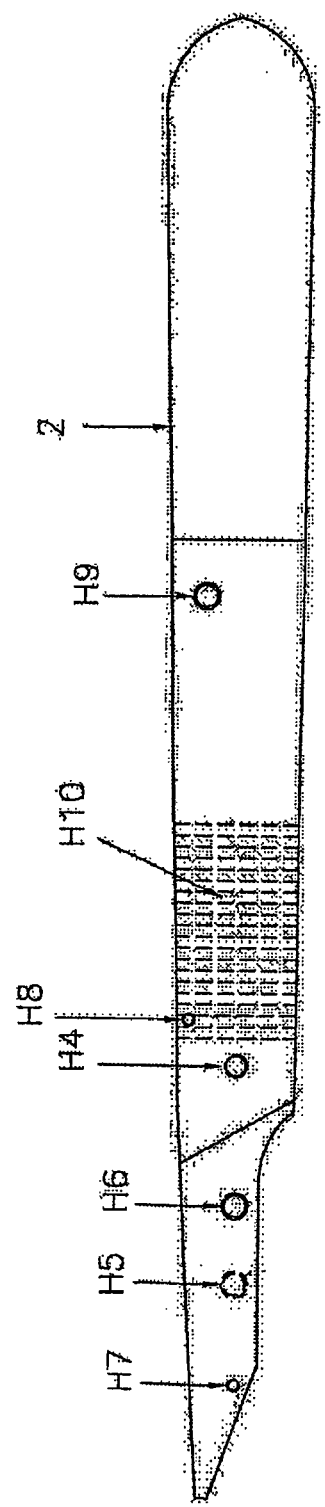
FIG. 3 is a schematic representation of the blade location arm showing holes required to fit various components of safe lock scalpels as in FIG. 2.

FIG. 3 is a schematic representation of the blade location arm showing holes required to fit various components of safe lock scalpels as in FIG. 2. The referenced details are given below:

i. Pivot pin hole (H4)
ii. Blade lock pin hole (H5)
iii. Blade locate pin hole (H6)
iv. Blade locate pin hole (H7)
v. Stopper pin hole for blade lock arm (H8)
vi. Lock pin hole for lock pin (H9)
vii. Thumb grip lines for left hander (H10)

Figure 4:
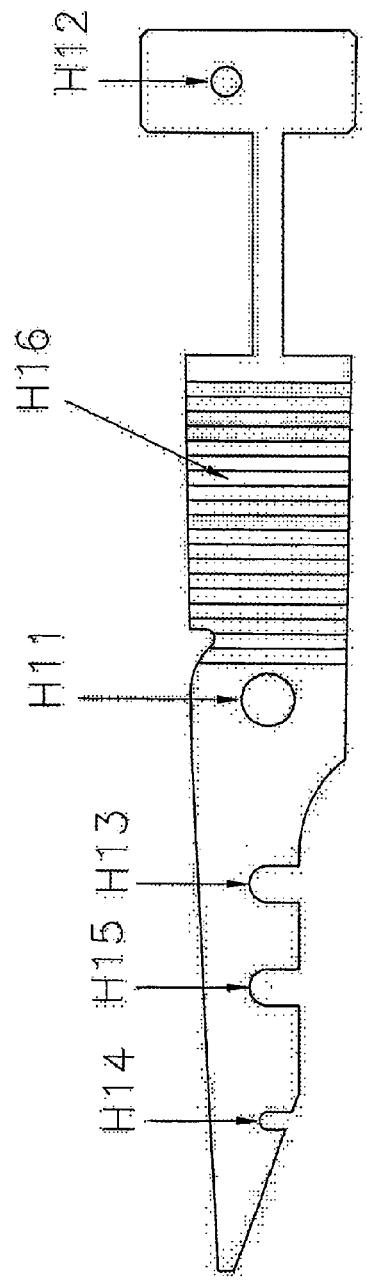
FIG. 4 is a schematic representation of the blade lock arm showing holes required to fit various components of safe lock scalpels as in FIG. 2).

FIG. 4 is a schematic representation of the blade lock arm showing holes required to fit various components of safe lock scalpels as in FIG. 2). Details are i. Pivot pin bearing hole (H11)
ii. Lock pin insert slot (H12)

iii. Locate pin rear (big) insert slot (H13)
iv. Locate pin rear (small) insert slot (H14)
v. Lock pin insert hole (H15)
vi. Thumb grip lines for right hander (H16)

Figure 5:
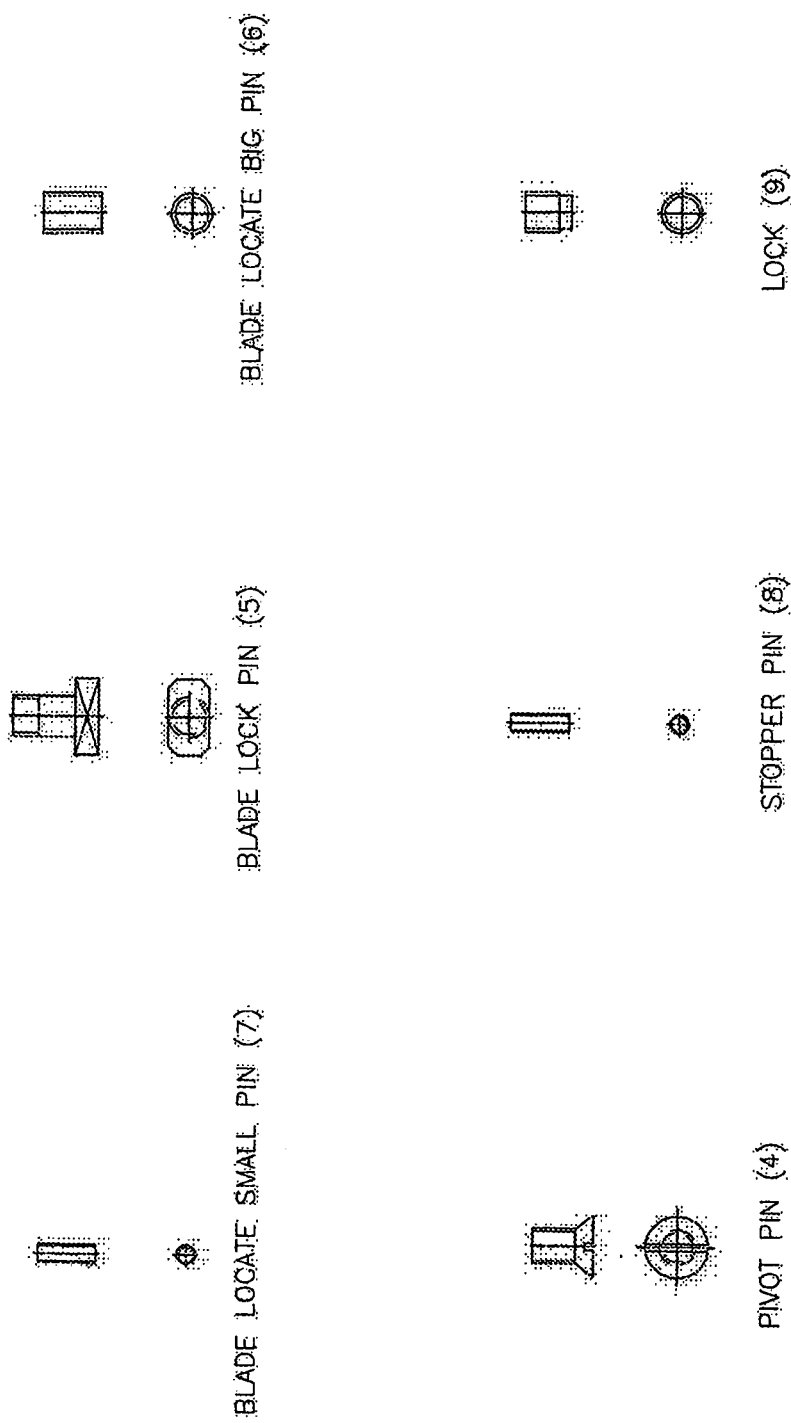
FIG. 5 is a representation of other components required in the handle of the invention.

FIG. 5 is a representation of other components required in the handle of the invention. These components have reference numbers 2,3,4,5,6,7,8, and 9.

The invention is explained through drawings as illustrated in FIG. 1 to FIG. 5. FIG. 1 depicts the handle of the invention in a state ready to use. The handle comprises of a blade holding arm (2) and a blade lock arm (3). These arms are depicted in greater detail in FIGS. 3 and 4 respectively. The components shown in FIG. 5 are the other components required to complete the assembly of invention. The blade holding arm (2) has drilled and tapped holes H4, H5, H6, H7, H8 and H9 to receive the pivot pin (4), a blade lock pin (5), a blade locating big pin (6), a blade locating small pin (7), a stopper pin (8), and a locking means (9) as shown in FIG. 5.

The blade lock pin (5), the blade locate big pin (6) and the blade locate small pin (7) are pins with different shapes and sizes and are fixed at front end of blade locating arm (2) to form a blade seat to locate the blade within tolerance fit. The drilled and tapped holes H4,H8 and H9 receive one or more pins to assist locking and stopper activity. The blade locking arm (3) functions as a lock and assists to complete the formation of scalpel in thickness, length and weight designed very close to standard metal scalpel to maintain same feel of user as per his present practice. The holes and slots H11, H12, H13, H14 and H15 are straight holes or half cut slots designed with tolerance required to receive the respective pins H4, H9, H6, H7 and H5. The blade lock pin (5) is constructed in order to lock and grip the blade firmly. The loading and unloading of blades before use and after use is depicted in FIG. 2. The blade insertion or removal is very simple with no exertion of force. The blade lock arm (3) is pivoted on the blade locating arm (2) with pivot pin 4 from position I and II. At position II the component 3 (blade lock arm) is stopped by stopper pin 9 so the blade seat gets fully open for insertion of blade. The lock arm is moved anti clockwise to enclose the blade with proper alignment with respect to component 2 (blade locate arm). The tail portion of lock arm 3 gets click locked with lock pin 9 and the scalpel is ready for use as shown in position I. In use position the blade is secured with both side support by locate arm and lock arm. This support does not allow the blade to bend and break even at excessive pressure used on hard tissues and bones. After use the blade can be disposed off in disposal box by lifting the lock arm tail and moving the arm clockwise. The blade can be detached from the handle by just inverting the handle and shaking till the blade drops into a disposal box or by using a forceps or like device. The blade locate arm as depicted in FIG. 3 is provided with thumb griff lines H10 for a left handed user. The blade lock arm (3) in FIG. 4 has thumb griff lines H16 for right handed user.

The device of the invention provides several advantages over prior art devices.

1. All standard surgical blades with ISO 7740:1985 can be used
2. The handle reinforces the back of the blade between its two arms and greatly reduces blade flex and risk of blade breakage. This avoids the use of special reinforced back blades which are expensive.
3. The handle can be disassembled to allow for complete cleaning and sterilisation. All parts of handle easy to reach and clean.
4. The blade is easily removable by simply turning over the handle, once the arms are opened. This blade will drop down.

It must be understood that variations and modifications are possible without departing from the spirit and scope of the invention in any manner.

The invention claimed is:

1. A universal blade handle comprising a blade locating arm and a blade lock arm, the blade locating arm being provided with a plurality of receiving means to receive a pivot pin, a blade lock pin, a first blade locating big pin bigger than a second blade locating small pin, a stopper pin, and a locking means, wherein the blade lock pin, the first blade locating big pin and the second blade locating small pin are provided at front end of the blade locating arm to form a blade seat to locate the blade, wherein the receiving means comprises a plurality of holes drilled and tapped into the blade locating arm, and wherein the blade lock arm functions as a lock with said receiving means, and wherein the receiving means comprise straight holes or half cut slots enabled to receive the corresponding pins.

2. The blade handle as claimed in claim 1, wherein the blade lock arm is pivotably mounted on the blade locating arm through the pivot pin.

3. The blade handle as claimed in claim 1, wherein the blade lock arm is movable from a first position to a second position wherein the blade lock arm is stopped by the stopper pin.

4. The blade handle as claimed in claim 1, wherein the blade lock arm is movable in a counter clockwise direction in order to enclose the blade with proper alignment with respect to the blade locating arm.

5. The blade handle as claimed in claim 1, wherein the blade lock arm is engageable with the lock pin at its tail portion.

6. The blade handle as claimed in claim 1, wherein the blade locating arm is provided with thumb griff lines.

* * * * *